United States Patent
Navelier et al.

(10) Patent No.: US 6,981,961 B1
(45) Date of Patent: *Jan. 3, 2006

(54) NEEDLELESS SYRINGE COMPRISING AN INJECTOR WITH NESTED ELEMENTS

(75) Inventors: Alain Navelier, Pierrefeu du Var (FR); Patrick Alexandre, Gray (FR); Bernard Brouquieres, Toulon (FR); Claude Mikler, Dijon (FR)

(73) Assignee: Crossject, Paris (FR)

( * ) Notice: Subject to any disclaimer, the term of this patent is extended or adjusted under 35 U.S.C. 154(b) by 374 days.

This patent is subject to a terminal disclaimer.

(21) Appl. No.: 10/018,133

(22) PCT Filed: Jun. 30, 2000

(86) PCT No.: PCT/FR00/01851

§ 371 (c)(1), (2), (4) Date: Dec. 18, 2001

(87) PCT Pub. No.: WO01/05454

PCT Pub. Date: Jan. 25, 2001

(30) Foreign Application Priority Data

Jul. 16, 1999 (FR) .................................. 99 09252

(51) Int. Cl.
*A61M 5/30* (2006.01)

(52) U.S. Cl. ........................................................ 604/68
(58) Field of Classification Search ............ 604/68–70, 604/93.01, 181, 187; 239/86, 88
See application file for complete search history.

(56) References Cited

U.S. PATENT DOCUMENTS

| 3,788,315 | A | | 1/1974 | Laurens |
| 4,068,801 | A | | 1/1978 | Leutheuser |
| 5,026,343 | A | | 6/1991 | Holzer |
| 5,074,843 | A | | 12/1991 | Dalto et al. |
| 5,630,796 | A | * | 5/1997 | Bellhouse et al. .......... 604/518 |
| 5,938,639 | A | * | 8/1999 | Reilly et al. ................ 604/131 |
| RE38,145 | E | * | 6/2003 | Lynn .......................... 604/537 |
| 6,623,446 | B1 | * | 9/2003 | Navelier et al. .............. 604/68 |

FOREIGN PATENT DOCUMENTS

| DE | 196 07 922 A1 | 9/1997 |
| EP | 0 370 571 A2 | 1/1989 |
| FR | 1 378 829 A | 2/1965 |
| JP | 6-312141 | 11/1994 |
| JP | 11-170533 | 6/1999 |

* cited by examiner

Primary Examiner—LoAn H. Thanh
(74) Attorney, Agent, or Firm—Oliff & Berridge, PLC

(57) ABSTRACT

The invention concerns the field of needleless syringes for injecting an active principle for therapeutic purposes. More particularly, it concerns a needleless syringe for injecting an active principle (7) initially set between an injector (1, 10) comprising at least an injection nozzle, said injector being contacted with the skin, and a wall (8) mobile under the effect of a propelling system (9) pressurizing and expelling the active principle through the injector located at the syringe downstream end (2). In order to produce nozzles in a considerable injector thickness and to control the jet coherence distance, said injector (1, 10) comprises at least two elements (3, 4) whereof the contact surfaces (30, 40, 40') are oriented towards the skin, at least a groove (31, 41, 41') forming an injection nozzle in the assembly of said elements.

11 Claims, 4 Drawing Sheets

US 6,981,961 B1

NEEDLELESS SYRINGE COMPRISING AN INJECTOR WITH NESTED ELEMENTS

BACKGROUND OF THE INVENTION

1. Field of Invention

The present invention is in the field of needleless syringes used for intradermic, subcutaneous and intramuscular injections of liquid active principle for therapeutic use in human or veterinary medicine.

In this field, to improve the effectiveness of the injection, use is made of syringes with, at their downstream part applied to the skin or very close to the skin of the subject, an injector comprising several ducts so that the liquid that is to be injected can be distributed to several points spread over a relatively large area. This solution also has the advantage of reducing the pain and eliminating any possible superficial or subcutaneous damage that might result from an excessive amount of liquid injected at a single point.

To improve the effectiveness of the injection, the shape of the jet is also altered: the coherent distance of the jet is controlled and a solution is sought that is someway between a highly coherent jet, such as used for jet cutting and which would have very deep penetration and would cause dangerous tearing of the skin, and a jet which nebulizes the liquid and thus the fine droplets do not penetrate the skin.

2. Description of Related Art

U.S. Pat. No. 3,802,430 describes a needleless syringe in which the liquid that is to be injected is discharged by a piston pushed by gases produced by a pyrotechnic generator; that syringe has five ducts which are parallel to the axis of the syringe and have circular cross sections. U.S. Pat. No. 3,788,315 describes a syringe in which the piston discharging the liquid is pushed by the expansion of compressed gases or of a compressed spring. That syringe has six ducts of circular cross sections and the axes of which diverge slightly from the axis of the syringe. In these examples, although the liquid is spread across several points, the ducts remain fairly close together; in addition, the simplicity of the shape of these ducts shows that these ducts are not optimized for controlling the coherent length of the jet which is itself an important factor in the performance of the injector in this particular application.

More generally, the problems posed by producing an injector for a syringe are problems of mechanical strength, of performance as we have just mentioned, and of cost.

Specifically, the injector, placed at the downstream part of the syringe, must not deform under the effect of the pressure of the liquid at the time of injection: the injector has to be relatively thick, and the more widely the ducts are spread over a large area, the thicker it has to be. The problem will be that of producing ducts which in general are very fine through great thicknesses.

The performance of the injector lies in the possibility of controlling the coherent distance of the jets leaving the ducts or nozzles, for predetermined conditions of use (nature of the liquid, injection pressure), through ducts of appropriate cross sections. The purpose of this appropriate cross section is to create a field of turbulence in the flow such that, a short distance from the exit from the injector, the jet remains coherent, that is to say is fine and fast-moving enough to pierce and penetrate the skin of the subject that is to be treated, and then the jet very quickly loses its coherency: it explodes to best diffuse the active principle under the skin. The problem is that of, in a simple way, producing not only fine ducts over great thicknesses but, above all, ducts with appropriate cross sections.

Finally, the cost of manufacture becomes a very important factor in the case of mass-produced syringes, particularly for disposable syringes.

SUMMARY OF THE INVENTION

The present invention relates to a needleless syringe for intradermic, subcutaneous or intramuscular injecting of a liquid active principle initially placed between, on the one hand, an injector comprising at least one injection nozzle, said injector being placed in contact with the skin or a very short distance away from the skin of the subject that is to be treated, and, on the other hand, a wall that can be displaced under the effect of a propulsive system pressurizing and expelling the active principle through the injector placed at the downstream end of the syringe, which is such that the injector consists of at least two elements the contacting surfaces of which are directed towards the skin, at least one of the contacting surfaces having at least one groove which constitutes an injection nozzle in the assembly of said elements.

In this invention, “liquid active principle” is essentially intended to mean a somewhat viscous liquid, or a mixture of liquids, or a gel. The active principle may be a solid placed in solution in an appropriate solvent for injection. The active principle may be a solid in pulverulent form placed in suspension, of greater or lesser concentration, in an appropriate liquid. The particle size of the solid active principle and the shape of the duct need to be matched to avoid the ducts becoming blocked.

One constituent element of the injector comprises a face which lies on the active principle side: this will be termed the upstream face, and a face located on the skin side: this will be termed the downstream face, and the lateral surface, all or some of which is in contact with all or some of the lateral surface of at least one other element. Over at least a portion of the lateral surface, at least one groove runs from the upstream face to the downstream face.

In the assembly of the constituent elements a groove may face the lateral surface of an adjacent element; it may also face another groove running along the lateral face of the other adjacent element; the grooves placed facing each other may have identical or different cross sections.

In the case of the injector of the syringe in a first configuration, the contacting surfaces of two adjacent elements, which contacting surfaces are wholly or partly lateral surfaces of said elements, are surfaces of revolution.

In a second configuration of the injector, the contacting surfaces of two adjacent elements, which contacting surfaces are wholly or partly lateral surfaces of said elements, are flat surfaces.

The transverse dimensions of a groove are very small with respect to the length of the groove. It may be said to a first approximation that the groove is positioned around the curve running along a portion of the lateral surface of a constituent element of the injector.

In a first embodiment, this curve running along the lateral face is roughly straight: the groove will be said to be straight. This is, for example, the case of a longitudinal groove made on a surface which is itself flat, or cylindrical or conical.

In a second embodiment, this curve running along the lateral face is not straight or is an oblique curve not contained in any plane, and the groove will be said to be helical. This is, for example, the case of a helical groove produced on a cylindrical or conical surface.

In a third embodiment, this groove is formed by the convergence of at least two groove portions beginning from the upstream face of the element and ending in a single groove portion towards the downstream face of the element. The various groove portions are straight or helical.

Advantageously, the groove has a cross section that is roughly constant when following the groove from the upstream face to the downstream face of the element. Its cross section is preferably of simple geometric shape, for example a V-shaped, U-shaped or semicircular groove. These shapes have a plane of symmetry which passes through an axis of symmetry of the element.

As a preference, the groove has an evolving cross section. When the groove is followed from the upstream face to the downstream face, its cross section varies or evolves, increasing or decreasing, uniformly or abruptly, so that the nozzle has a succession of tubular parts and of cavities, an appropriate arrangement of these various parts making it possible to master and control the jet coherent distance according to predetermined conditions of use: viscosity of the liquid that is to be injected, injection pressure, in particular.

Such an evolving cross section is, for example, achieved simply from a groove of constant cross section, like the one previously described, on which is superposed at least one recess which locally widens and deepens the groove. In the assembly of the elements of the injector, said recesses will create cavities along the injection nozzle which will be of evolving cross section, this arrangement making it possible to control the jet coherent distance.

The convergence of at least two grooves into a single groove may also achieve the evolving cross section as it is to be understood here.

Finally, the groove may be a succession of recesses very close together which constitute the groove of evolving cross section.

In a first embodiment of the needleless syringe, the injector includes a support comprising at least one housing into which an element which constitutes a one-piece core is fitted. Said core and support comprising grooves to produce at least one injection nozzle.

In the second embodiment of the needleless syringe, the injector comprises at least one core consisting of at least two elements or quarters assembled via their flat faces to form at least one nozzle of evolving cross section, the elements or quarters of the various cores being fitted into housings of a support.

For these two embodiments, a fitting-together is preferably a forced press fit which also ensures sealing at the contacting surfaces.

The one-piece core or the core made up of several quarters either exhibit symmetry of revolution; the core has the shape of a cylinder or of a cone frustum, or symmetry of repetition of order n: the core has the shape of a prism or of a pyramid frustum. Obviously, the housing that accommodates the core has the same shape, it has a mating shape so that the two can be fitted together.

In a third embodiment of the needleless syringe, the injector comprises at least one core consisting of at least two quarters assembled by their flat faces to form at least one nozzle with an evolving cross section, the quarters of the various cores being held together by overmolding.

Nested assemblies, in which a subassembly comprising a support of overmolding equipped with their cores also forms part of the invention. The preferred nested assembly is the one that consists of the fitting-together of a core into a support having one single housing, this fitted-together assembly acting as a core for another support with one single housing. One particularly simple embodiment consists in fitting a core directly into the downstream end of the syringe formed for this purpose.

Advantageously, in the case of elements of truncated shape such as cone frustums, pyramid frustums or quarters of such elements, construction and assembly will be performed in such a way that the downstream face is that of the smallest cross section: through this assembly, the pressure of the liquid will have a tendency to fit the elements together rather than driving them out of their housings.

The present invention also relates to an injector such that said injector consists of at least two elements the contacting surfaces of which are directed towards the skin, at least one of the contacting surfaces comprising at least one groove which constitutes an injection nozzle in the assembly of said elements.

A syringe according to the invention solves the problems posed. In terms of the strength of the injector, the increase in the thickness presents no difficulties with regard to producing fine ducts with evolving or non-evolving cross sections over great thicknesses.

In terms of the performance of the injector, the invention makes it possible in a simple way, in order so that it can be adapted to predetermined conditions of use, to control the coherence distance of the jets leaving the nozzles.

In terms of the cost aspect, the injector has relatively simple shapes which are easy to produce, by directly molding the elements of the injector or by machining grooves and recesses into blanks produced elsewhere. All of these manufacturing and assembly operations lend themselves to a high degree of automation.

The syringe according to the invention additionally has an undeniable advantage from the point of view of safety in the event of abnormal use. For example, if the syringe is directed towards the face and triggered accidentally, the jets will have no effect other than to shower said face with active principle, without any mechanical piercing effect, as long as the syringe is not in contact with (or very close to) the face. This advantage is associated with the mastery of the jet coherence distance.

BRIEF DESCRIPTION OF THE DRAWINGS

The present invention will be described in greater detail with the aid of the following figures.

DETAILED DESCRIPTION OF PREFERRED EMBODIMENTS

Figure 1:
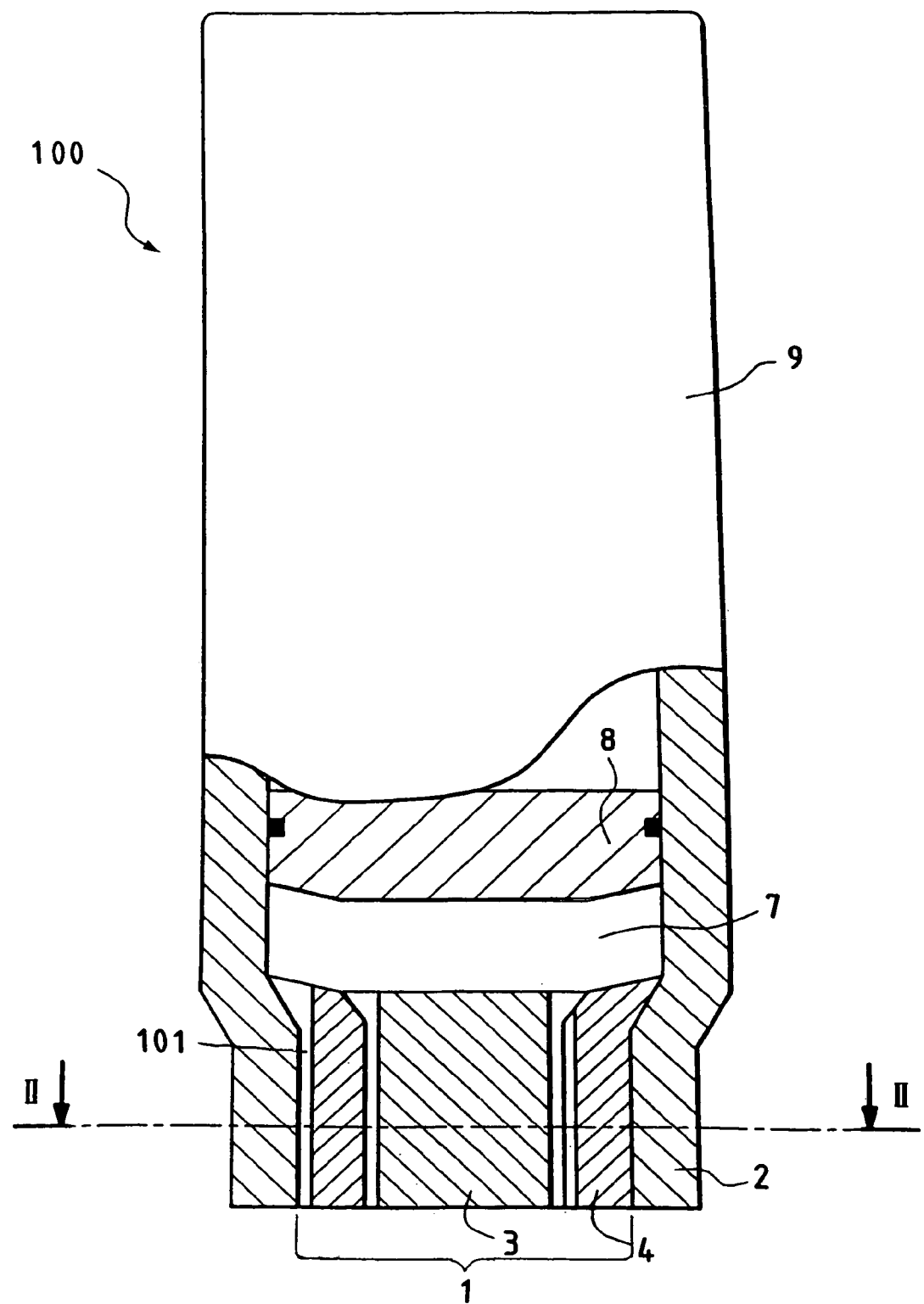
FIG. 1 depicts, in longitudinal part section, a syringe according to the invention.

FIG. 1 schematically depicts a needleless syringe 100 for injecting liquid active principle. Such a syringe is generally cylindrical and has a reservoir containing the active principle 7. This reservoir is closed at one end, which we have called the downstream end 2, by an injector 1 comprising at least one duct or one injection nozzle 101. This injector generally rests against the skin of the subject that is to be treated, or is held a very short distance away from the skin, the skin not being depicted in this drawing. This injector is located at the end of the reservoir and includes an essentially cylindrical support 4 and a core 3 fixed to this end of the reservoir by appropriate means. The other end of the reservoir is closed by a displaceable wall, for example a piston 8 comprising means for providing sealing, such as an O-ring. Finally, the syringe comprises a propulsive system 9 with a triggering device for displacing the piston and injecting the liquid. Among the propulsive systems that can be used and without going into detail thereof, we may mention a pyrotechnic gas generator as described in U.S. Pat. No. 3,802, 430 already mentioned, we also mention the expansion of a compressed gas or the compressed spring, as described in U.S. Pat. No. 3,788,315. Obviously, the syringes according to the invention may be fitted with any one of these types of propulsion system for displacing the piston.

The injector 1 (see also FIG. 2) is forcibly press fitted into the end 2 of the syringe. This injector comprises an essentially cylindrical support 4 with an exterior lateral face 40 resting against the interior lateral face 20 of the end of the syringe and an interior lateral face 40' against which the exterior lateral face 30 of a core 3, in this example a one-piece core, comes into contact. The support 4 and the core 3 each have, on the upstream side, a shoulder which serves to immobilize and wedge these three elements 3 and 4 in the assembly; the shoulder is, in this example, frustoconical. The grooves on the exterior lateral walls continue into the frustoconical shoulder.

Figure 2:
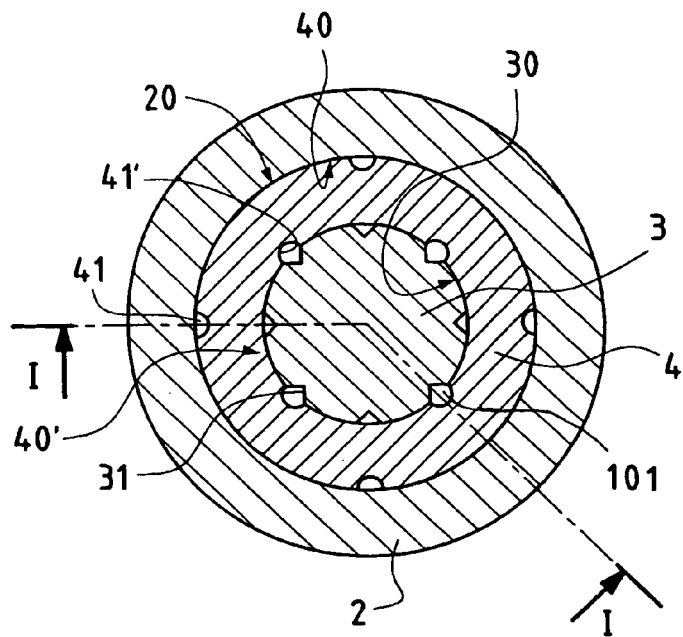
FIG. 2 depicts, in cross section, the injector of said syringe.

FIG. 2 depicts, in cross section, the downstream end 2 of the previously described syringe. The support 4 is fitted into the end 2 of the syringe, the contacting faces being, respectively, the lateral faces 40 and 20'. Fitted inside the support 4 is a core 3, the contacting faces being, respectively, the lateral faces 40' and 30. The exterior lateral face 40 of the support 4 has four grooves, such as the groove 41, and these are uniformly distributed and have roughly the shape of a semicircle, said grooves facing the lateral surface 20 of the downstream end 2 of the syringe. The interior lateral face 40' of the support 4 also comprises four grooves, such as the groove 41', similar to the previous ones, also uniformly distributed but offset by 45° with respect to the outer grooves. Finally, the lateral face 30 of the core 3 has eight grooves, such as the groove 31, these being uniformly distributed and having a V-shaped cross section. Of these grooves, every second one faces a groove such as the groove 41', the other grooves facing the interior lateral wall 40' of the support.

The grooves on the exterior lateral walls, grooves such as the grooves 31 or 41, continuing to the frustoconical shoulder of the core 3 and of the support 4. The grooves on an interior lateral face such as the groove 41' are in the continuation of the opening in the shoulder of the groove such as 31 placed facing it.

The transverse dimensions of the grooves are such that they correspond to circular orifices with equivalent diameters of 0.05 mm to 0.5 mm. The height of an element injector is between about 3 mm and about 10 mm. Finally, the orifices of the grooves are distributed around concentric circles, the diameters of which are between 3 mm and 30 mm.

Figure 3:
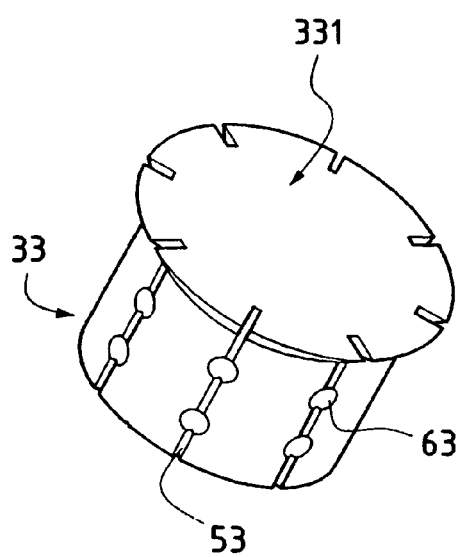
FIGS. 3 and 4 depict, in perspective, types of cores that can be used in the injector of the syringe previously depicted.

FIG. 3 depicts a core 33 viewed in perspective. This core is mounted on a support of the type depicted in the previous figures.

The core 33 is essentially circular and cylindrical, and on the upstream side has a frustoconical shoulder, the upstream face 331 of which is visible. The lateral surface of the core has eight grooves 53 distributed uniformly, these are longitudinal and of semicircular cross section; these grooves continue into the shoulder. On each groove there are two conical recesses 63 which locally widen and deepen the groove. When this core is fitted into a housing of a support, these grooves and recesses will produce a nozzle of evolving cross section comprising, in this example, two cavities which will generate turbulence in the jet and thus allow the jet coherence distance to be controlled.

In this example, the core, over a circular part, has a diameter of 8 mm and its overall height (including shoulder) is 5.8 mm; the grooves are of semicylindrical shape, the radius being 0.1 mm, the cones having the vertex angle of 90° and a circular base 1 mm in diameter.

Figure 4:
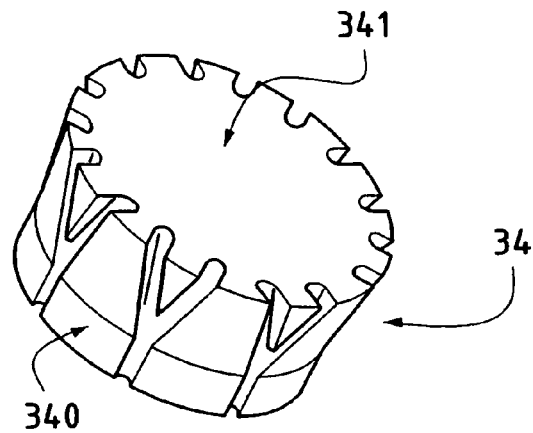

FIG. 4 depicts another core 34 viewed in perspective.

This core, the geometry of which is of revolution, is the combination of the frustoconical part at the upstream end and of a cylindrical part at the downstream end, this combination of shapes ensuring that the core is self-immobilized in its housing. The lateral surface 340 of the core has eight groups of uniformly distributed grooves. The cross section of the grooves is U-shaped. On the frustoconical part of the lateral surface 340, starting from the upstream face 341, two identical groove portions converge to join together as a single groove, with the same cross section on the cylindrical part of the lateral surface so as to open onto the downstream face. In this example, the shear at the confluence of two flows will generate the turbulence that controls the jet coherence distance.

Figure 5:
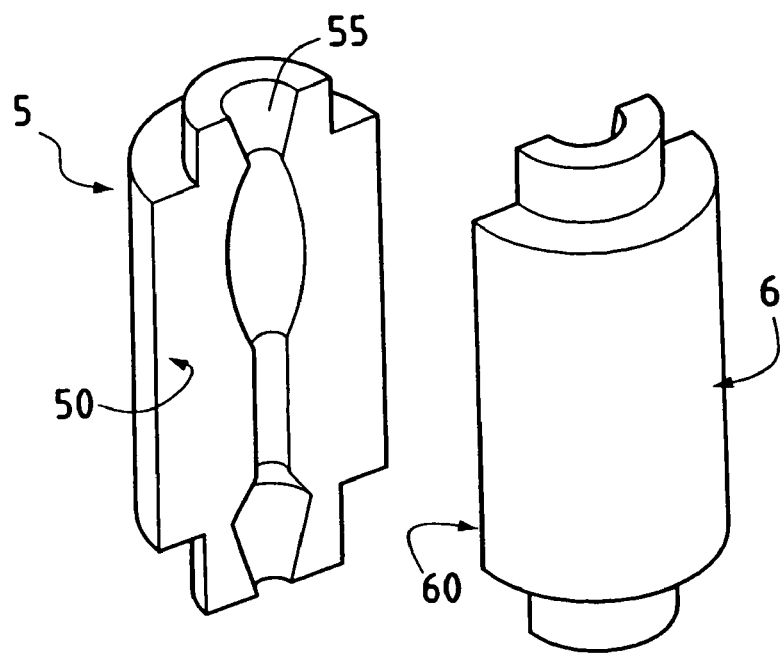
FIG. 5 depicts, viewed in perspective, two elements of a core according to another embodiment of the invention.

FIG. 5 depicts, in perspective, a core consisting of several parts or quarters, in this example two parts 5 and 6 essentially in the shape of two half-cylinders depicted with a marked separation to make the diagram more legible. These two half-cylinders 5 and 6 will be back to back via their flat faces 50 and 60 (the latter is hidden in the case of the element 6). In this example, each flat face has, at its middle, a groove of evolving cross section. Given that its appearance differs slightly from what has already been described, we shall also call it a recess, but said recess is really a groove with evolving cross section according to the invention.

Figure 6:
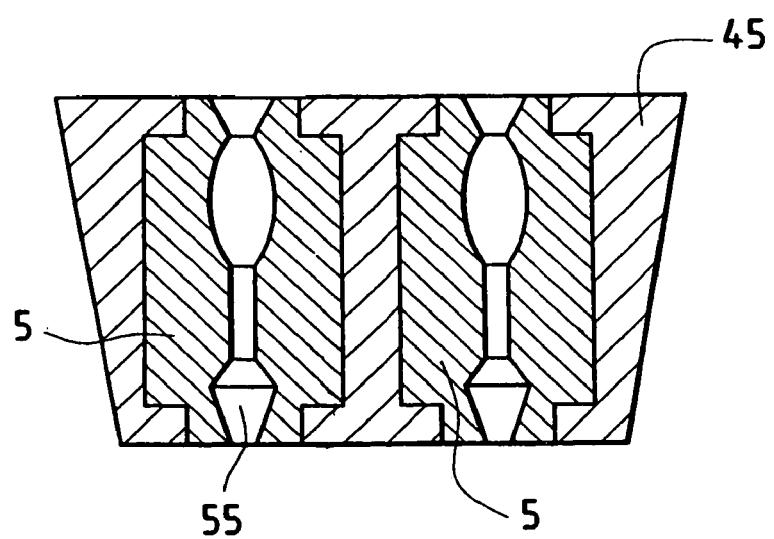
FIG. 6 depicts, in longitudinal section, a syringe injector obtained by assembling elements of the type of those depicted in FIG. 5.

FIG. 6 depicts, in cross section, an injector 10 consisting of two cores comprising two parts 5, 6 assembled in an overmolding 45; the parts 5, 6 have, at their two ends, a portion of smaller diameter which forms shoulders for centering the elements in the overmolding. In the assembly of the quarters such as 5 and 6, the recesses facing each other form a duct 55 with symmetry of revolution and evolving cross section comprising, in this example, from the upstream face to the downstream face, a cone frustum meeting an oblong cavity followed by a circular cylindrical portion connecting to a cavity formed by two unequal cone frustums joined by their largest bases.

In general, the thickness of an element of the injector, this being the distance from the upstream face to the downstream face, is between about 3 mm and about 10 mm. The dimensions of the cross sections of the grooves or the recesses evolve and are such that the area corresponds to that of a circular duct of a diameter varying between about 50 $\mu$m and 1000 $\mu$m.

Figure 7:
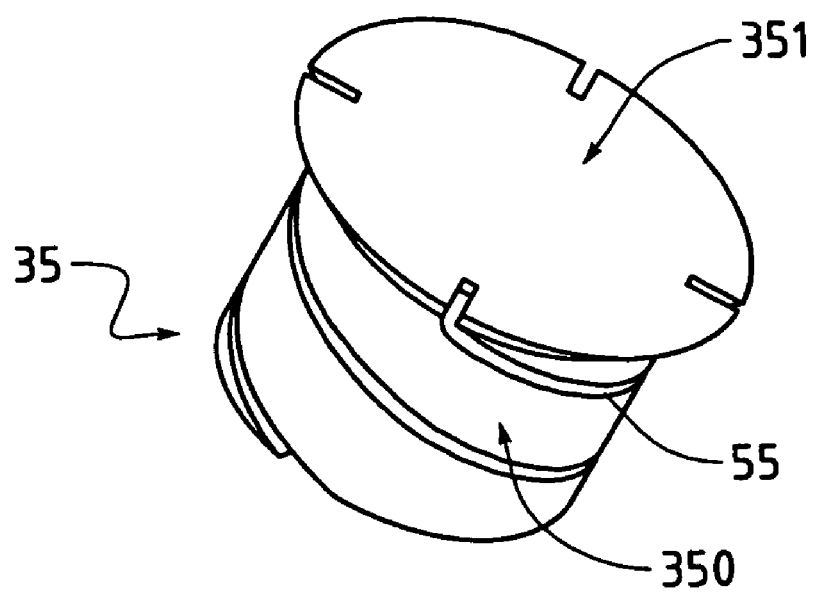
FIG. 7 depicts, in perspective, a type of core that can be used in the injector of the syringe previously depicted.

FIG. 7 depicts a core 35 viewed in perspective. This core can be mounted on a support of the type depicted in FIGS. 1 and 2. The core 35 is essentially circular and cylindrical, and on the upstream side has a frustoconical shoulder, the upstream face 351 of which is visible. The lateral surface 350 of the core 35 has helical grooves 55 (only one groove shown) of semicircular cross section, and the helical grooves 55 continue into the shoulder. When this core 35 is fitted into a housing of a support, these grooves 55 will produce nozzles.

The materials for producing the syringe and the various parts of the nozzle will be chosen from materials which are compatible and approved for medical use; without claiming to be exhaustive, we quote by way of example plastics materials such as polycarbonate, polytetrafluoroethylenes; metals, stainless steel, or glass for medical use type I or II.

What is claimed is:

1. A needleless syringe for injecting an active principle, comprising:
   an injector including at least one injection nozzle, said injector being placed a distal end of the needleless syringe; and
   a wall that can be displaced under the effect of a propulsive system pressurizing and expelling the active principle through the injector, wherein:
   the active principle is initially placed between the injector and the wall, and
   the injector includes an assembly of at least two elements; each of said elements having a downstream face, an upstream face and a lateral surface joining said elements together, the lateral surfaces of said elements in the assembly being at least partly in contact with each other to define contacting surfaces; at least one of the lateral surfaces having at least one groove which constitutes the injection nozzle in the assembly of said elements; and the injection nozzle being located between the lateral surfaces.

2. The needleless syringe according to claim 1, wherein the contacting surfaces are non-planar surfaces.

3. The needleless syringe according to claim 1, wherein the contacting surfaces are planar surfaces.

4. The needleless syringe according to claim 1, wherein the groove is straight.

5. The needleless syringe according to claim 1, wherein the groove is helical.

6. The needleless syringe as claimed in claim 1, wherein the groove is formed by the convergence of at least two grooves beginning from the upstream face and ending in a single groove towards the downstream face of the element.

7. The needleless syringe according to claim 4, wherein the groove has a constant cross section.

8. The needleless syringe according to claim 4, wherein the groove has an evolving cross section.

9. The needleless syringe according to claim 1, wherein said elements comprise a support and a one-piece core, the one-piece core being fitted into the support.

10. The needleless syringe according to claim 1, wherein said elements comprise a support and at least one core, the at least one core having at least two parts, each of the at least two parts having a flat face and being assembled via the flat faces to form the at least one core with the nozzle of evolving cross section, the parts of the at least one core being fitted into the support.

11. The needleless syringe according to claim 1, wherein said elements comprise a support and at least two cores, each of the at least two cores comprising at least two parts, each of the at least two parts having a flat face, the flat faces being assembled to form each of the at least two cores with the nozzle having an evolving cross section, and the parts of the at least two cores being held together by overmolding.

\* \* \* \* \*